| United States Patent [19] | [11] Patent Number: 5,032,582 |
| Abra | [45] Date of Patent: Jul. 16, 1991 |

[54] METHOD FOR TREATING FUNGAL INFECTIONS WITH AMPHOTERICIN B/CHOLESTEROL SULFATE COMPOSITION

[75] Inventor: Robert Abra, San Francisco, Calif.

[73] Assignee: Liposome Technology, Inc., Menlo Park, Calif.

[21] Appl. No.: 320,354

[22] Filed: Mar. 8, 1989

Related U.S. Application Data

[63] Continuation of Ser. No. 19,575, Feb. 27, 1987, Pat. No. 4,822,777.

[51] Int. Cl.$^5$ .......................... A61K 31/70; C07H 1/00
[52] U.S. Cl. ........................................ 514/31; 536/6.5; 536/16.8; 536/18.5
[58] Field of Search .................. 514/31; 536/6.5, 16.8, 536/18.5

[56] References Cited

U.S. PATENT DOCUMENTS 4,468,513  8/1984  Kirst et al. ..................... 536/16.8
4,822,777  4/1989  Abra ................................. 514/31

*Primary Examiner*—Elli Peselev
*Attorney, Agent, or Firm*—Hana Dolezalova

[57] ABSTRACT

An amphotericin B composition containing particles of amphotericin B and cholesterol sulfate, in a molar ratio of between about 1:1 to 1:4. The particles, when stored in lyophilized form and reconstituted in an aqueous suspension, have particle sizes predominantly between aobut 100–400 nm. The composition formed at a molar ratio of about 1:1 amphotericin B:cholesterol sulfate has stable particle sizes in an aqueous suspension over a several-day storage period. The composition is significantly less toxic and more effective in treating fungal infections than prior amphotericin B formulations.

6 Claims, No Drawings

METHOD FOR TREATING FUNGAL INFECTIONS WITH AMPHOTERICIN B/CHOLESTEROL SULFATE COMPOSITION

This is a continuation of U.S. patent application entitled AMPHOTERICIN B/CHOLESTEROL SULFATE COMPOSITION AND METHOD, Ser. No. 019,575 filed Feb. 27, 1987 now U.S. Pat. No. 4,822,777.

FIELD OF THE INVENTION

The present invention relates to an amphotericin B composition for the treatment of fungal infections, and in particular, to an amphotericin B composition which has both a high $LD_{50}$ and therapeutic efficacy.

REFERENCES

1. Holz, R. W., in F. E. Hahn, Ed., Antibiotics, Vol.2, Springer-Verlag, N.Y. (1979).
2. Trembley, C., et al. Antimicrob. Agents and Chemoth. 26(2):170(1984).
3. Mehta, R. T., et al. Infection and Immunity, 47(2):429 (1985).
4. Lopez-Berestein, G., et al. Cancer Drug Delivery, 1(1):37 (1983).
5. New, R.R.C., et al. J. Antimicrob. Chemoth. 8:371 (1981).
6. Graybill, J. R., et al. J. Infect. Dis., 145:5 (1982).
7. Lopez-Berestein, G., J. Infect. Dis., 150(2):278 (1984).
8. Trembley, C., et al. Invest. Opthalmol. 26:711 (1985).
9. Lopez-Berestein, G., et al. J. Infect. Dis. 151(4):704 (1985).
10. Juliano, R., et al. Biology of the Cell, 4(39) (1983).
11. Mehta, R., Et al, Biochem. Biophys Acta. 770:230 (1984).
12. Hopfer, R. L., et al. Antimicrob. Agents and Chemoth. 25(3):387 (1984).
13. Brockerhoff, H. et al. Biochimica Biophysica Acta 691:227 (1982).
14. Crowe, L. M., et al. Biochimica Biophysica Acta 769:141 (1984).
15. Remington's Pharmaceutical Sciences, Gennaro, A. R., ed., Mack Publishing Company (1985)

BACKGROUND OF THE INVENTION

Amphotericin B (AMB) is an effective antifungal agent, and at present, is the drug of choice for most serious systemic fungal infections (reference 1). The drug is presently available for human use as a lypholized powder of AMB and deoxycholate ("Fungizone"). The drug binds strongly to ergosterol, a major sterol component of fungal membranes, forming pores in the membranes which allow leakage of solute molecules. The drug also has a strong binding affinity for cholesterol, a sterol present in most mammalian cell membranes, and is therefore capable of disrupting host cells.

When AMB is administered in free form (i.e., as a reconstituted AMB/deoxycholate complex) side effects resulting from red blood cell disruption are observed initially, followed by more serious cardiotoxicity, CNS and bone-marrow effects. Renal toxicity, resulting from the body's attempt to clear the drug, is also present.

Several studies have shown that AMB toxicity can be reduced by administering the drug in a liposome-bound form (references 2-12). Typically, the $LD_{50}$ of the drug increases from about 2-3 mg/kg body weight for the free drug up to about 8-15 mg/kg when the drug is administered in liposomal form. One limitation of liposomal formulations, however, is the apparent size instability of amphotericin B/liposomal particles when stored in an aqueous medium. Typically, AMB-containing liposomes which have an initial size distribution between about 200-300 nm will spontaneously form large liposomal structures of up to several microns on long-term storage in an aqueous medium. Liposomes with sizes greater than about 1-2 microns are generally more toxic than smaller liposomes when administered parenterally, i.e., into the bloodstream. The toxicity of large liposomes in the bloodstream is related in part to liposome blockage of the alveolar capillaries. There are also indications that relatively large liposomes are more toxic to the liver, presumably due to liposome accumulation in reticuloendothelial cells. Co-owned U.S. patent application for "Amphotericin B Liposome Composition", Ser. No. 781,395, filed Sept. 27, 1985, discloses a novel method of preparing and storing AMB liposomes which largely overcome the size-growth problem mentioned above.

An amphotericin B composition formed by complexing AMB with a polyethylene derivative of cholesterol (PEG-cholesterol) has also been proposed (PCT application US84/00855). The formulation increased the $LD_{50}$ of AMB to 10.0 mg/kg in mice, from 3.8 mg/kg for Fungizone, and was also less cytotoxic in cell culture. It is not known how and whether AMB complexing to PEG-cholesterol affects therapeutic efficacy against fungal infection in vivo, nor whether the complex can be stored in a size-stable form.

SUMMARY OF THE INVENTION

One object of the invention to provide an AMB i composition which has a substantially higher $LD_{50}$ than AMB formulations reported in the prior art, and also is significantly more effective in treating fungal infections, in vivo.

Another object of the invention is to provide an AMB formulation which can be stored in suspension form over a several day period without significant particle size change, which can be stored long term as a lyophilized preparation.

Yet another object of the invention is to provide an improved method for treated fungal infections with AMB.

The invention includes an AMB composition containing particles of AMB and cholesterol sulfate, in a mole ratio of AMB to cholesterol sulfate of between about 1:1 to 1:4. When prepared in a suspension form in an aqueous medium, the particles have preferred sizes between about 100-400 nm. Osmotic swelling and solute trapping studies indicate that the particles are non-liposomal. A preferred composition, containing AMB and cholesterol sulfate in a mole ration of about 1:1 shows very little change in particle size when stored in solution form over a several-day period.

The composition is formed, according to one aspect of the invention, by dispersing an aqueous suspension of amphotericin B/cholesterol sulfate particles, in a molar ration of between 1:1 to 1:4, to optical clarity, where particle sizes are predominantly between 100-200 nm. The suspension is then lyophilized in the presence of a cryoprotectant, such as lactose. After reconstitution in an aqueous medium, particle sizes are predominantly in the range 200-300 nm.

The composition has an $LD_{50}$ greater than 20 mg/kg. The therapeutic efficacy of the AMB/cholesterol sulfate composition, in treating fungal infections in vivo, is significantly greater than that observed for Fungizone.

The invention also includes a method for treating fungal infections with AMB, with substantially less toxicity and greater efficacy than has been achieved heretofore.

These and other objects and features of the invention will become more fully apparent from the following detailed description of the invention.

DETAILED DESCRIPTION OF THE INVENTION

I. Preparation of the Particle Composition

A. Particle Suspension

To prepare the AMB/cholesterol sulfate particle suspension of the invention, AMB and cholesterol sulfate are combined in dry or solution form at a selected mole ration of AMB to cholesterol sulfate about 1:1 to 1:4. In a preferred method, the two components are mixed in dry form, at the selected mole ration, than dissolved in a suitable solvent, and preferably an alcohol such as methanol. A combined molarity of AMB and cholesterol sulfate in methanol of 50 umole/ml, in the mole ratio range between 1:1 and 1:4 AMB to cholesterol, is suitable. For example, in a 1:1 formulation, both AMB and cholesterol sulfate would be present at 25 umoles/ml.

A cryoprotectant may be added to the AMB/cholesterol sulfate solution, to a final preferred concentration of between about 5-15%. The cryoprotectant serves two purposes in later processing steps. First, it provides a crystalline, water-soluble bulking agent on which the AMB and cholesterol sulfate components can form, when the solvent in the mixture is removed. That is, the dried crystals of cryoprotectant increase the surface area of lipid film formed on solvent removal, and this facilitates particle hydration when an aqueous medium is added to dried mixture. Secondly, where the hydrated particles are stored in a lyophilized state, as discussed below, the cryoprotectant may reduce particle damage which can occur on freezing, and thereby reduce size growth of the rehydrated particles. Suitable cryoprotectants are carbohydrates such as trehalose, lactose, maltose, cellobiose, sucrose, glucose, fructose, sorbitol, raffinose, myo-inositol, and glycerol (references 14) which have also been shown effective in limiting lipid membrane damage on freezing (reference 14). A variety of other water-soluble bulking agents, such as maltodextrin, salts and the like may be substituted for cryoprotectant where particle processing does not involve a freezing step, such as where the particles are dried for storing by spray drying.

The lipid solution of AMB/cholesterol sulfate is dried to a lipid film. As just indicated, the film is preferably formed from a solution containing a bulking agent, yielding dried particles of the agent coated with the lipid mixture. Solvent removal is by vacuum evaporation or under a stream of inert gas, e.g., nitrogen. The dried lipid film may be stored under an inert gas, preferably at 4° C. or less.

An aqueous particle suspension if formed by addition of an aqueous medium to the dried lipid mixture. The medium used in Example 1, containing 10 mM Tris-HCl, 0.1 mM EDTA, pH 7.4, is suitable. The amount of medium added is sufficient to produce a final AMb concentration of preferably between about 25-100 umole/ml.

Initially, the lipid material is crudely suspended by spatula or mechanical agitation until the lipid clumps are released into the aqueous medium, to form a slurry-like mixture. This material is now dispersed to a fine particle size by sonication, homogenization, French press or other high-energy input. The dispersion is carried out until a desire particle size, preferably between 0.1 to 1 micron is achieved. The suspension may be warmed during dispersion, and should be maintained under an inert atmosphere. In the method described in Example 1, the suspension is sonicated at 4° C. to optical clarity. Final particle sizes were between 0.1-0.2 microns. Here it is noted that formulations containing less than about 1 mole cholesterol sulfate per mole AMB do not sonicate to optical clarity, indicating that particle dispersion requires at least a stoichiometric amount of cholesterol sulfate.

The particle suspension may be treated such as any molecular sieve chromatography or dialysis, to remove traces of unincorporated AMB. The dialysis conditions noted in Example 1 are suitable The final concentration of AMB in the dispersed particle suspension can be determined by diluting an aliquot of the suspension in methanol, and measuring AMB spectrophotometrically at 406 nm. Typical AMB concentrations at various stages of the preparation of the dispersion are given in Table 1 in Example 1 below.

B. Dried Particle Suspension

According to one aspect of the invention, it has been discovered that the AMB/cholesterol sulfate particles of the invention can be stored long-term in dried form without significant increase in particle size or rehydration.

The dried particle formulation can be prepared either by lyophilization or spray drying. In the former method, the small-particle suspension is quick frozen and lypohilizied at shelf temperature of preferably 20° C. or less, as described in Example I. The effect of lyophilizing on particle size is seen in Table 2 in Example 2, for each of four formulations having AMB:-cholesterol sulfate mole ratios between 1:1 and 1:4. In each case, mean particle sizes increased from about 100-200 nm before lyophilization, to between 200-300 after lyophilization and rehydration with water. The stability of the particles, pre and post lyophilization is considered in Section II below.

For spray drying, the particle suspension is dried in a conventional apparatus in which the particles to be dried are sprayed in aerosolized suspension form into a stream of heated air or inert gas, and the aerosolized droplets are dried in the gas stream as they are carried toward a plate collector where the dried liposomes are collected. An exemplary spray dry apparatus is a Buchi 190 Mini Spray Dryer.

The drying temperature is at least about 37° C., and preferably between about 40°-50° C. The temperature of the collection chamber is generally lower than that of the heated air, and typically about 37° C. The dried particles are collected and stored in dehydrated form, under an inert atmosphere.

II. Size Stability

This section examines the size stability of AMB:-cholesterol particle suspensions under a variety of conditions relating to molar composition of the particles, suspension medium, and storage time.

In the first study, reported in Example 3, AMB: cholesterol sulfate particles having mole ratios of AMB:-cholesterol sulfate of 1:1, 1:2, 1:3, and 1:4 were prepared and immediately after dialysis were stored for periods of up to 8 days at 4° C. The results are shown in Table 3 of Example 3. The 1:1 formulation was substantially stable over the 8-day test period, whereas the other formulations showed progressively greater size increases with increasing mole ratios of cholesterol sulfate.

The size stability of the same four formulations after lyophilization and rehydration was similarly studied, also as reported in Example 3. Size stability data for the eight day test is shown in Table 3. Interestingly, there was little difference in size stability amount the four formulations, and for each formulation mean particle sizes increased at most about 2 fold over 4 the eight day test period. The combined results from Tables 2 and demonstrate that (a) lyophilized AMB/cholesterol particles can be reconstituted with little increase in mean size and size distribution and (b) the particles in the reconstituted suspension are relatively stable on storage in solution over a several-day period.

The effect of physiological-strength saline and plasma on the size characteristics of the particles was also examined, as reported in Example 4. In a first study, the four post-dialysis AMB/cholesterol sulfate formulations from above were diluted in 0.9% saline, and the particle sizes examined immediately thereafter. As shown in the top row in Table 5, all of the particles showed a large size increase, although the 1:1 formulation was less aggregated. A similar study on post-lyophilization particles was also carried out, with the results shown in the top row of Table 6 in Example 4. A comparison of Tables 5 and 6 data shows that the 1:1 formulation is substantially more size stable in saline after lyophilization than post-dialysis. The other three formulations, having greater cholesterol sulfate mole ratios, showed large size increases in saline both pre and post lyophilization.

A second study was designed to examine AMB/-cholesterol sulfate particle size in blood plasma, and the effect of subsequent dilution of the plasma medium with suspending buffer. Initially, each of the four samples (both pre and post lyophilization) were diluted 1:1 with human plasma, then diluted after a few minutes with suspending buffer containing 10% lactose. Size measurements were made immediately after dilution, and again 20 minutes later. The results are shown in the bottom two rows of Tables 5 and 6 in Example 4. Summarizing the data, plasma caused a size increase in all of the formulations. Smallest size increases were seen in the 1:1 formulation, where particle sizes were less than 1 micron (1,000 nm). The size increase produced on contact with plasma was at least partially reversible for all formulations except the 1:4 formulation, as evidenced by the significant reduction in particle size after 20 minutes incubation in dilute form in suspension medium. There was little difference in the size behavior of particles in pre- and post-lyophilization formulations.

The data above demonstrate that the AMB:cholesterol sulfate formulation of the invention can be stored in dried form long term, without significant increase in size, on rehydration, or significant change in size stability in plasma. One significant advantage of the dried particles which was observed was substantially greater size stability on storage in buffer. Within the range of AMB: cholesterol sulfate mole ratios which was examined, the 1:1 formulation, gave greatest size stability and smallest mean particle sizes under the various conditions examined.

III. Particle Characteristics

It has been reported that cholesterol sulfate is capable of forming lipid vesicles or liposomes on extended (several hour) sonication (reference 13). It was therefore of interest to determine whether the AMB u cholesterol sulfate particles of the present invention are liposomal in form. For these studies, the 1:4 AMB/cholesterol sulfate formulation was selected, since a relatively high ratio of cholesterol sulfate is more likely to form liposomal structures.

One characteristic of liposomes is a continuous lipid bilayer capable of encapsulating water-soluble solute molecules. Many water-soluble molecules, such as sugars and other marker solutes, are readily encapsulated in liposomes by preparing (dispersing) the liposomal lipids in an aqueous medium containing the marker solute. Smaller marker molecules, such as sugars, also tends to pass through lipid bilayer membranes slowly, as evidenced by equilibration of the solute between encapsulated and bulk phase aqueous compartments over a several-hour to several-day solute-exchange period.

To test the ability of AMB/cholesterol sulfate (1:4) particles to encapsulate sucrose, the particles were prepared by dispersion in a medium containing $^{14}C$ sucrose. After sonication to optical clarity, the particles were separated from the suspending medium by molecular sieve chromatography, using a column sieving material which excludes particles in the size range of the AMB/-cholesterol sulfate particles. Details of the test were given in Exmaple 5. Briefly, 95% of the AMB was associated with the particles eluted in the void volume, but no detectable peak of radioactivity was associated with the particles.

Based on this study, it appears that the particles do not form encapsulating (liposomal) structure, or alternatively, that the particles form very leaky structures. The latter explanation is unlikely, since (a) cholesterol tends to decrease permeability in liposomes to small water-soluble permeants, and (b) the pure cholesterol derivative liposomes which have been described (reference 13) have very low permeability. Studies on cholesterol hemisuccinate liposomes also show stable encapsulation of a variety of small water-soluble molecules (PCT patent application WO 05030).

Another characteristic feature of liposomes is the ability of isotonic liposomes to swell on injection into a hypotonic medium. Here the liposomes are acting as small osmometers in response solute gradients across the bilayer membranes. Isotonic liposome swelling has been observed in liposome prepared from a variety of cholesterol derivatives, including cholesterol-PEG and cholesterol sulfate (reference 13) and cholesterol hemisuccinate liposomes (PCT patent application WO 85/05030). Cholesterol-derivative liposomes show the expected increased absorbance when injected into increasingly dilute media, although these liposomes behave less like ideal osmometers than do liposomes formed from conventional phospholipid components.

Each of the above four AMB/cholesterol particle compositions from above (1:1, 1:2, 1:3, and 1:4 mole ratios) was prepared in 10% lactose. Both pre- and post dialysis particles were tested for osmotic swelling in distilled water, comparing particle size immediately after dilution with particle size 20 minutes after dilution.

The results are shown in Table 7 in Exmaple 6. No swelling was observed in any of the particle formulations. The test supports the finding from the encapsulation studies above that the AMB/cholesterol sulfate particles of the invention do not form closed vesicle structures.

IV. Therapeutic Uses

AMB is useful in treating a variety of systemic fungal organisms, including coccidiomycosis, cryptococcosis, systemic moniliasis, histoplasmosis, aspergillosis, rhodoptorulosis, sporotrichosis, phycomycosis, and blastomycosis, and is also effective against some species of Leishmania (reference 15). Because of the server side effects of the drug, in its presently available free form, it is generally administered only to patients with progressive, potentially fatal systemic fungal infections, and the patient must remain hospitalized during drug treatment for constant monitoring of renal function.

This section describes the increased toxicity and improved efficacy of AMB in the present formulation, and the potential therefore of wider drug use, particularly for prophylactic use in preventing opportunistic fungal infection in immune-deficient or immune-compromised patients, such as those receiving cancer chemotherapy, immunosuppressive drugs, or radiation therapy.

A. AMB/Cholesterol Sulfate Toxicity

According to an important feature of the invention, it has been discovered that the AMB:cholesterol sulfate composition described herein is substantially less toxic than free AMB (Fungizone), as evidenced by a much higher $LD_{50}$ value. Further, the composition is considerably less toxic than liposomal or lipid-complex forms of AMB which have been described in the prior art, as judged by a comparison with reported $LD_{50}$ values. Toxicity studies to determine $LD_{50}$ values for the composition of the invention are detailed in Example 7. An initial test examined the lethal toxicity of Fungazone and 1:4 AMB/cholesterol sulfate particles. Based on the data shown in Table 8, the $LD_{50}$ of the free AMB (Fungizone) composition is between 1–4 mg/kg animal weight. This value is increased to between 15–25 mg/kg in the amb/cholesterol sulfate composition. $LD_{50}$ value is substantially higher than values previously reported for liposomal or lipid-complex AMB formulations described in the prior art.

In the second test, also reported in example 8, the lethal toxicity of the four different mole ratio AMB formulation described above, at a dose of 20 mg/kg was investigated. Surprisingly, it was found that the 1:1 formulation was non-lethal at the 20 mg/kg in all six test animals, indicating an $LD_{50}$ value of substantially above 20 mg/kg. The data show that the $LD_{50}$ for the other three formulations is less than 20 mg/kg, and at least for the 1:4 formulation, therefore between 15–20 mg/kg.

The composition also enjoys the advantage that cholesterol sulfate is a natural cholesterol component found widely in animals. The cholesterol compound has no known toxicity, and is metabolized in the body by cholesterol sulfatase.

Finally, since toxicity is expected to increase with increased particle size, the stable and relatively small particles which can be injected may contribute to reduced toxicity.

B. Efficacy

Another important feature of the AMB/cholesterol sulfate composition is significantly enhanced drug efficacy in treating systemic fungal infection. One efficacy study performed in support of the present invention is detailed in Example 9. Here animals infected intravenously with *C. albicans* were treated with Fungizone, at doses between 0.3 and 0.9 mg/kg body weight, or with 1:4 AMB:cholesterol sulfate, at doses between 0.3 and 2.0 mg/kg. Drug efficacy was determined by survival at 25 days post-drug administration. The data, presented in Table 10, show that the AMB/cholesterol sulfate composition gives significantly higher survival rates at each dose level between 0.3 and 0.9 mg/kg. At 2.0 mg/kg, all of the animals treated with the formulation of the invention survived.

C. Modes of Administration

The present invention provides a dehydrated AMB composition which, when rehydrated after an extended storage period, forms a suspension of AMB particles having a selected size range less than about 1 micron. Because the particles can be stored in an anhydrous, inert environment, toxicity and lipid and drug breakdown problems related to oxidation and mechanical damage at a gas/liquid interface are minimized. For parenteral use, e.g., intravenous administration, the composition is preferably formed from AMB liposomes having sizes of between about 0.1 to 0.4 microns, such as can be prepared by the methods above. The AMB-/lipid composition is hydrated typically to a selected AMB concentration between about 50 and 200 mg/ml, and administered at a concentration of between 1 and 5 mg AMB/kg body weight.

Where the drug is given intramuscularly, to provide slow drug release from the site of injection, the composition is preferably rehydrated to a more concentrated form, which can be conveniently localized in an injection site.

From the foregoing, it can be appreciated how various objects and features of the invention are met. The invention provides an AMP formulation which has substantially reduced toxicity and greater drug efficacy and free AMP or lipid/AMP formulations described in the prior art. The enhanced therapeutic index of the drug, particularly related to reduced toxicity, allows much wider use of the drug, for example, for prophylactic treatment of immune-compromised patients, and also provides greater therapeutic efficacy, in the treatment of active systemic fungal infections.

The composition is readily prepared, and the cholesterol sulfate component is relatively inexpensive in purified form, and naturally utilized when administered parenterally. The formulation is easily stored in dried form, and when rehydrated, yields a particle suspension with selected small sizes.

The following examples illustrate methods of preparing, characterizing, and using the AMB/cholesterol sulfate composition of the invention. The examples are in no way intended to limit the scope of the invention.

Materials $CHSO_4$ (cholesterol 3-sulphate, sodium salt) was obtained from Sigma Chemical Co., St. Louis, Mo.; AMB (amphotericin-B, Type 1) was donated by E.R. Squibb & Sons, Inc., (Batch No. 20-914-5978-001). All other materials are of reagent grade or superior from commercial sources.

EXAMPLE 1

Preparation of AMB/CHSO4 Particles

AMB and CHSO4 in dry powder form were weighed out and combined to give one of the four AMB:cholesterol sulfate mole ratios listed in Table 1 below. The amount of AMB and cholesterol sulfate added was sufficient to produce a final AMB plus cholesterol sulfate concentration in the particle suspension of about 50 umole/ml.

Dry methanol was added to the AMB/cholesterol sulfate powder to a final AMB concentration of between 0.2–0.6 mg/ml, and the suspension was stirred until all of the powder dissolved. Lactose was added to this solution to produce a 10% (w/v) lactose solution in the final aqueous product. The solution was dried in vacuo, yielding dried lactose particles coated with a lipophilic AMB/cholesterol sulfate film.

A suspending buffer containing 10 mM Tris-HCl, 0.1 mM EDTA pH 7.4, 67 mOsm, was added to the dried mixture in an amount sufficient to produce a final AMB plus cholesterol sulfate concentration of 50 umole/ml. This suspension was sonicated with an Ultrasonic Liquid Processor (Heat Ultrasonics, Inc., Farmingdale, N.Y.), Model W-800, probe sonicator until the suspension becomes optically clear. (This process is facilitated if the suspension is warmed to 45° C. in a water bath.) Sonication was performed under nitrogen gas.

The sonicated AMB/CHSO4 particles were dialyzed to remove traces of unincorporated AMB, using 6000–8000 molecular weight cut-off dialysis tubing. The material was dialyzed against a buffer containing 10 mM Tris-HCl, 0.1 mM EDTA, 10% (w/v) lactose, pH 7.4, 300 mOsm. The clear suspension was dried by rapid freezing in a dry ice/isopropanol mixture and lyophilized overnight at a shelf temperature of −25° C., followed by a further two hours at 25° C. (15 SRC-X Lyophilizer; Virtis, Gardiner, N.Y.). Lyophilized samples were reconstituted by addition of an equal volume of water and gentle mixing. Table 1 below shows the AMB concentrations of the four compositions, at various stages of preparation.

TABLE 1

| | AMB Concentration (mg/ml) | | | |
|---|---|---|---|---|
| Molar Ratio | Theoretical | Pre-Dialysis | Post-Dialysis | Post-Lyophilization/Rehydration |
| 1:1 | 23.10 | 20.66 | 24.20 | 21.52 |
| 1:2 | 15.40 | 10.80 | 16.46 | 15.19 |
| 1:3 | 11.55 | 11.02 | 12.19 | 11.60 |
| 1:4 | 9.24 | 9.49 | 10.12 | 8.79 |

EXAMPLE 2

Effect of Lyophilization on Particle Size

Particle sizes were determined by dynamic laser-light scattering using a Nicomp Model 200 sizer (Nicomp Instruments Inc., Goleta, Calif.). Samples were typically diluted to 0.3 umole/ml for this measurement using 10 mM Tris/HCl, 0.1 mM EDTA, 10% (w/v) lactose buffer, pH 7.4. The mean particle sizes and standard deviations (S.D.) for the four compositions from Example 1 are given in Table 2 below. As seen, all four compositions have mean particle sizes between about 130–180 nm prior to lyophilization, and between about 210–280 nm after lyophilization.

TABLE 2

| Molar Ratio AMB/CHSO4 | Particle Diameter Particles Immediately Post-Dialysis | (mean ± S.D. nm) Particles Post-Lyophilization/Rehydration |
|---|---|---|
| 1:1 | 138 ± 54 | 268 ± 137 |
| 1:2 | 148 ± 66 | 211 ± 105 |
| 1:3 | 172 ± 89 | 265 ± 147 |
| 1:4 | 138 ± 61 | 274 ± 151 |

EXAMPLE 3

Effect of Storage in Solution On Particle Size

The four samples from Example 1, each containing an AMB plus cholesterol sulfate concentration of about 50 umole/ml, were incubated at 4° C. for up to eight days. At days 0, 2, 6 and 8, an aliquot of each suspension was withdrawn, diluted to about 0.3 umole/ml, and examined for particle size distribution, as in Example 2. The results are shown in Table 2 below. It is seen that 1:1 composition is stable to particle size change, whereas the compositions containing higher molar amounts of cholesterol sulfate are progressively less table on storage.

TABLE 3

| Days of Storage | Particle Diameter (mean ± S.D. nm) as a Function of AMB/CHSO4/Molar Ratio Post-Dialysis) | | | |
|---|---|---|---|---|
| | 1:1 | 1:2 | 1:3 | 1:4 |
| 0 | 138 ± 54 | 148 ± 66 | 172 ± 89 | 138 ± 61 |
| 2 | 193 ± 98 | 336 ± 194 | 527 ± 299 | 334 ± 192 |
| 6 | 161 ± 82 | 462 ± 265 | 679 ± 377 | 823 ± 481 |
| 8 | 179 ± 95 | 512 ± 296 | 968 ± 551 | 1034 ± 587 |

A similar stability study was performed on the same compositions after lyophilization and reconstitution in distilled water, as in Example 1. The results, given in Table 4, show (1) relatively small size increases over the eight day test for each of the four compositions, and (b) little effect on size changes of the molar amount of cholesterol sulfate.

TABLE 4

| Days of Storage | Particle Size (mean ± S.D. nm) as a Function of AMB/CHSO4 Molar Ratio (Post-Lyophilization) | | | |
|---|---|---|---|---|
| | 1:1 | 1:2 | 1:3 | 1:4 |
| 0 | 268 ± 137 | 211 ± 105 | 265 ± 147 | 279 ± 151 |
| 2 | 304 ± 153 | 331 ± 177 | 541 ± 293 | 554 ± 303 |
| 6 | 340 ± 171 | 418 ± 224 | 515 ± 283 | 478 ± 242 |
| 8 | 371 ± 188 | 436 ± 228 | 570 ± 314 | 487 ± 258 |

EXAMPLE 4

Effect of Saline and Plasma on Particle Size

The four samples from Example were diluted to approximately 0.3 umole/ml with 0.9% (w/v) saline and their sizes measured as in Example 2. The results are shown at the top line in Table 5 below. For each formulation, saline produced a more than tenfold increase in mean particle size. The size growth of the 1:1 composition was substantially less than for the three compositions with greater amounts of cholesterol sulfate.

The four samples were also diluted 1:1 (v/v) with human plasma and subsequently (within a few minutes of contact with the plasma) diluted with 10 mM Tris/HCl, 0.1 mM EDTA, 10% lactose (w/v) buffer pH 7.4, for sizing. Size measurements, reported in Table 5 below, were made immediately after diluting, and 20 minutes after diluting. The data indicate that the 1:1 formulation is least sensitive to size change, upon contact with plasma, and that for all formulations, incubation in the diluted medium for 20 minutes produced some size decrease.

TABLE 5

| Treatment | Particle Size (mean ± S.D. nm) as a Function of AMB/CHSO$_4$ Molar Ratio (Post-Dialysis) | | | |
|---|---|---|---|---|
| | 1:1 | 1:2 | 1:3 | 1:4 |
| Dilute in saline | 3328 ± 1990 | 13209 ± 8288 | 6789 ± 4276 | 11072 ± 6618 |
| Mix + plasma, dilute + suspending buffer | 728 ± 334 | 1200 ± 628 | 4017 ± 1951 | 1942 ± 1043 |
| 20 minutes later | 358 ± 169 | 823 ± 457 | 1745 ± 1007 | 1667 ± 942 |

Similar size measurements, after mixing with 0.9% saline or plasma, were made on AMB/cholesterol sulfate particles after lyophilization and rehydration with distilled water, as in Example 1. The results are shown in Table 6 below. Size changes similar to those observed with pre-lyophilized particles (Table 5 date) were observed.

TABLE 6

| Treatment | Particle Size (mean ± S.D. nm) as a Function of AMB CHSO$_4$ Molar Ratio (Post-Lyophilization/Hydration) | | | |
|---|---|---|---|---|
| | 1:1 | 1:2 | 1:3 | 1:4 |
| Dilute in saline | 1738 ± 1007 | 8405 ± 5549 | 13158 ± 8625 | 9813 ± 6265 |
| Mix + plasma, dilute + suspending buffer | 955 ± 466 | 1030 ± 550 | 1766 ± 976 | 2467 ± 1233 |
| 20 minutes later | 534 ± 267 | 776 ± 378 | 1147 ± 643 | 2661 ± 1374 |

EXAMPLE 5

Particle Encapsulation Studies

The ability of the AMB/cholesterol sulfate particles to encapsulate a radiolabeled marker was examined. CHSO$_4$/AMB, 4:1 molar ratio particles, were prepared as in Example 1, except that the Tris buffer medium used to suspend the dried AMB/cholesterol sulfate mix contained 1 uCi of $^{14}$C-sucrose. The suspension was applied to a Sephadex G50 gel exclusion column equilibrated with 10 mM Tris/HCl, 0.1 mM EDTA, 10% (w/v) lactose buffer, pH 7.4, and the applied material was eluted with the same buffer. The particles were eluted in the void volume, which was monitored by UV absorption at 280 nm. The samples were collected and examined for radioactivity by conventional scintillation counting. It was found that 95% of the AMB was in the particle peak, whereas no detectable peak of $^{14}$C-sucrose occurred in this region.

EXAMPLE 6

Osmotic Swelling Studies

CHSO$_4$/AMB formulations containing the four different mole ratios of AMB and cholesterol sulfate were prepared as in Example 1, (in the usual suspension medium containing 10% lactose). These samples are designated as post-dialysis (P.D.) suspensions in Table 7 below. A portion of each sample (containing 10% lactose) was lyophilized and reconstituted in distilled water, and these samples are designated as lyophilized and reconstituted (L.R.) in the table.

The P.D. and L.R. samples were each diluted to 0.3 umole/ml with distilled water, and the size distribution of the particles immediately after dilution in the hyptonic medium, and 20 minutes after dilution was measured as in Example 2. The results are given in Table 7 below. As seen, there is no appreciable swelling, over a 20 minute incubation period, as evidenced by an increase in mean particle size, in any of the samples examined.

TABLE 7

| Molar Ratio AMB/CHSO$_4$ | Sample Post-Dialysis (PD) or Post-Lyophilization/Rehydration (LR) | Time (min) | Particle Size (mean ± S.D. nm) |
|---|---|---|---|
| 1:1 | PD | 0 | 109 ± 42 |
| | | 20 | 114 ± 45 |
| 1:1 | LR | 0 | 212 ± 107 |
| | | 20 | 212 ± 105 |
| 1:2 | PD | 0 | 126 ± 59 |
| | | 20 | 134 ± 64 |
| 1:2 | LR | 0 | 170 ± 81 |
| | | 20 | 184 ± 89 |
| 1:3 | PD | 0 | 124 ± 58 |
| | | 20 | 131 ± 61 |
| 1:3 | LR | 0 | 205 ± 117 |
| | | 20 | 204 ± 107 |
| 1:4 | PD | 0 | 161 ± 86 |
| | | 20 | 185 ± 100 |
| 1:4 | LR | 0 | 228 ± 116 |
| | | 20 | 236 ± 122 |

EXAMPLE 7

Toxicity (LD$_{50}$) of the Particle Suspensions

Outbred male Swiss/Webster mice were obtained from Simonsen Labs, Inc. The animals weighed approximately 15–45 grams on the day of treatment and were between 4–8 weeks old. The animals were quarantined for at least three days prior to the study, and only mice that remained healthy during the quarantine period were used. The animals were given food and water ad libitum.

In a first study, the animal groups were treated with either Fungizone (Squibb) suspended in sterile saline or 1:4 AMB/cholesterol sulfate composition prepared as in Example 1. In each case, the AMB concentration was adjusted such that the selected dose of AMB (given in Table 8) could be administered in a final volume of 0.2 ml. Forty-eight animals were employed for each dose group. The test material was administered by a single intravenous injection via the lateral tail vein. Each dose was administered over about 1.5 minutes.

The animals were observed for signs of toxicity and death at least three times (1, 2, and 4 hour post treatment) on the day of treatment. During the remaining observation period of five days, the animals were examined daily in the morning and afternoon. The test results, expressed as the ratio of number of survivors on day five:total number of animals treated, are given in Table 8. The $LD_{50}$ value for Fungizone, calculated by conventional methods, is 3.2 mg/kg. The $LD_{50}$ for the AMB/cholesterol sulfate composition between 15-20 mg/kg.

TABLE 8

| Treatment | Number of Survivors on Day 5 (Post-Injection/Total Animals Injected) |
|---|---|
| FUNGIZONE | |
| 0.5 mg/kg | 8/8 |
| 1.0 mg/kg | 8/8 |
| 2.0 mg/kg | 8/8 |
| 4.0 mg/kg | 2/8 |
| 6.0 mg/kg | 0/8 |
| 8.0 mg/kg | 0/4 |
| CHSO$_4$/AMB (4:1) | |
| 10 mg/kg | 3/3 |
| 15 mg/kg | 3/4 |
| 20 mg/kg | 2/5 |
| 25 mg/kg | 1/3 |

In a second toxicity test, mice were treated with 20 mg/kg of one of the four AMB/cholesterol sulfate formulations from Example 1, with drug administration and animal monitoring being done as above. The results, presented below in Table 9, show that the 1:1 formulation has an $LD_{50}$ value higher than 20 mg/kg.

TABLE 9

| Treatment (AMB/CHSO$_4$) | Number of Survivors on Day 5 (Post-Injection/Total Animals Injected) |
|---|---|
| 1:1 molar ratio | 6/6 |
| 1:2 molar ratio | 0/5 |
| 1:3 molar ratio | 1/5 |
| 1:4 molar ratio | 0/5 |

EXAMPLE 8

Efficacy of the AMB/Cholesterol Sulfate Formulation

Crl:CFW (SW)BR mice weighing 20-25 grams were obtained from the Charles River Breeding Laboratories, and were given food and water ad libitum. *C. albicans* strain 30 was grown at 35° C. on SDA (Sabourand Dextrose A gas) for 18 hours, and the organism is harvested and diluted with sterile nonpyrogenic saline to yield about $7 \times 10^8$ colony forming units in a 0.2 ml volume.

Eight-ten animals were injected in the tail vein each with 0.2 ml of the above *C. albicans* mixture. Two days after the fungal injection, the animals were injected with graded doses of Fungizone or AMB/cholesterol sulfate (1:4) prepared as in Example 1. The AMB preparations were adjusted in concentration so that each animal received a total volume, administered intravenously through the tail vein, of 0.1 ml. The amount of AMB administered, expressed in terms of mg drug/kg body weight of the animal is given at the left in Table 10. The animals were followed for 25 days post-drug administration. The number of survivors at 25 days per total number of test animals is shown in the table for the two AMB preparations, and a buffer control.

TABLE 10

| | Survivors Post-25 Days/Total Animals Injected | | |
|---|---|---|---|
| Dose | Free AMB | CHSO$_4$/AMB = 4:1 | Control |
| 0.0 mg/kg | — | — | 0/11 |
| 0.3 mg/kg | 2/10 | 5/10 | — |
| 0.6 mg/kg | 1/10 | 9/10 | — |
| 0.9 mg/kg | 3/10 | 9/10 | — |
| 2.0 mg/kg | — | 10/10 | — |

Although the invention has been described and illustrated with respect to specific embodiments, uses and methods of preparation, it will be appreciated that a variety of changes and modifications may be made without departing from the scope of the invention.

It is claimed:

1. A method of treating fungal infections in a mammal which method comprises administering to a mammal in need of such treatment a therapeutically effective amount of antifungal composition comprising particles containing, suspended in an aqueous medium, Amphotericin B and cholesterol sulfate, at a mole ratio of about 1:1 to 1:4.

2. The method of claim 1 wherein the composition particle size is upon reconstitution about 100-400 nm.

3. The method of claim 2 wherein the composition administered to a mammal is hydrated to a Amphotericin B concentration between 50 and 200 mg/ml and administered at a concentration of between 1 and 5 mg of Amphotericin B per kg of body weight.

4. The method of claim 3 wherein the composition is administered intravenously.

5. A process of preparing Amphotericin B composition by steps:
   (a) dispersing an aqueous suspension of Amphotericin B and cholesterol sulfate, in a molar ratio of between 1:1 to 1:4, to optical clarity with particle sizes predominantly between 100 and 200 nm;
   (b) lyophilizing the suspension of step (a) in the presence of a cryoprotectant before the particle sizes in the suspension increase substantially; and
   (c) reconstituting the lyophilized material with an aqueous medium to obtain a suspension of particles of sizes predominantly no larger than 400 nm;

said Amphotericin B composition comprising Amphotericin B and cholesterol sulfate having a $LD_{50}$ greater than about 15 mg/kg, which composition is able to prevent, during the lyophilization in the presence of the cyoprotectant, the increase of particles in the suspension to a size larger than 400 nm and which can be reconstituted with an aqueous medium to particle sizes between about 100-400 nm.

6. The process of claim 5, wherein the molar ratio of Amphotericin B to cholesterol sulfate in the suspension is about 1:1.

* * * * *